(12) United States Patent  
Umekawa et al.

(10) Patent No.: US 9,089,290 B2  
(45) Date of Patent: Jul. 28, 2015

(54) OPHTHALMOLOGIC APPARATUS, OPHTHALMOLOGIC CONTROL METHOD, AND PROGRAM

(71) Applicant: CANON KABUSHIKI KAISHA, Tokyo (JP)

(72) Inventors: Kazuaki Umekawa, Machida (JP); Tomoyuki Ikegami, Hiratsuka (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/055,301

(22) Filed: Oct. 16, 2013

(65) Prior Publication Data

US 2014/0111766 A1    Apr. 24, 2014

(30) Foreign Application Priority Data

Oct. 18, 2012    (JP) .................................. 2012-230783

(51) Int. Cl.
| | |
|---|---|
| *A61B 3/14* | (2006.01) |
| *A61B 3/00* | (2006.01) |
| *A61B 3/103* | (2006.01) |
| *A61B 3/12* | (2006.01) |

(52) U.S. Cl.
CPC . *A61B 3/14* (2013.01); *A61B 3/103* (2013.01); *A61B 3/12* (2013.01)

(58) Field of Classification Search
USPC ................................................. 351/200–246
See application file for complete search history.

(56) References Cited

U.S. PATENT DOCUMENTS

| | | | | |
|---|---|---|---|---|
| 8,534,836 | B2* | 9/2013 | Inoue et al. .................... | 351/206 |
| 8,636,362 | B2* | 1/2014 | Iwanaga ......................... | 351/206 |
| 8,693,749 | B2* | 4/2014 | Nakano .......................... | 382/128 |
| 8,861,817 | B2* | 10/2014 | Imamura et al. .............. | 382/128 |
| 8,899,749 | B2* | 12/2014 | Imamura ....................... | 351/206 |
| 2005/0270488 | A1 | 12/2005 | Hanebuchi | |
| 2006/0244911 | A1 | 11/2006 | Shimizu et al. | |
| 2008/0158508 | A1 | 7/2008 | Kawashima et al. | |
| 2013/0258284 | A1* | 10/2013 | Makihira et al. .............. | 351/206 |
| 2013/0321769 | A1* | 12/2013 | Kusumoto .................... | 351/206 |
| 2014/0111772 | A1* | 4/2014 | Ikegami ........................ | 351/211 |

FOREIGN PATENT DOCUMENTS

| | | |
|---|---|---|
| CN | 1810202 A | 8/2006 |
| CN | 1838908 A | 9/2006 |
| CN | 101254090 A | 9/2008 |
| CN | 102085089 A | 6/2011 |
| JP | 2004-033379 A | 2/2004 |
| JP | 4545871 B2 | 9/2010 |
| JP | 2012-183123 A | 9/2012 |

* cited by examiner

*Primary Examiner* — Mohammed Hasan

(74) *Attorney, Agent, or Firm* — Canon USA Inc. IP Division

(57) ABSTRACT

An ophthalmologic apparatus includes a projection unit configured to project a light flux to a subject's eye, an imaging optical system configured to form an image of the light flux reflected by the subject's eye or an image of the subject's eye on an imaging plane, an imaging unit provided on the imaging plane of the imaging optical system, a determination unit configured to determine a parameter regarding the imaging unit or the projection unit for acquiring unique information of the subject's eye based on a physical property of the subject's eye, and an acquisition unit configured to acquire the unique information based on the image of the light flux or the image of the subject's eye captured by the imaging unit with use of the determined parameter.

21 Claims, 9 Drawing Sheets

ALIGNMENT IS ESTABLISHED IN Z-AXIS DIRECTION (FRONT-BACK DIRECTION)

ALIGNMENT IS FAULTY IN Z-AXIS DIRECTION (FRONT-BACK DIRECTION) (TOO FAR AWAY)

ALIGNMENT IS FAULTY IN Z-AXIS DIRECTION (FRONT-BACK DIRECTION) (TOO CLOSE)

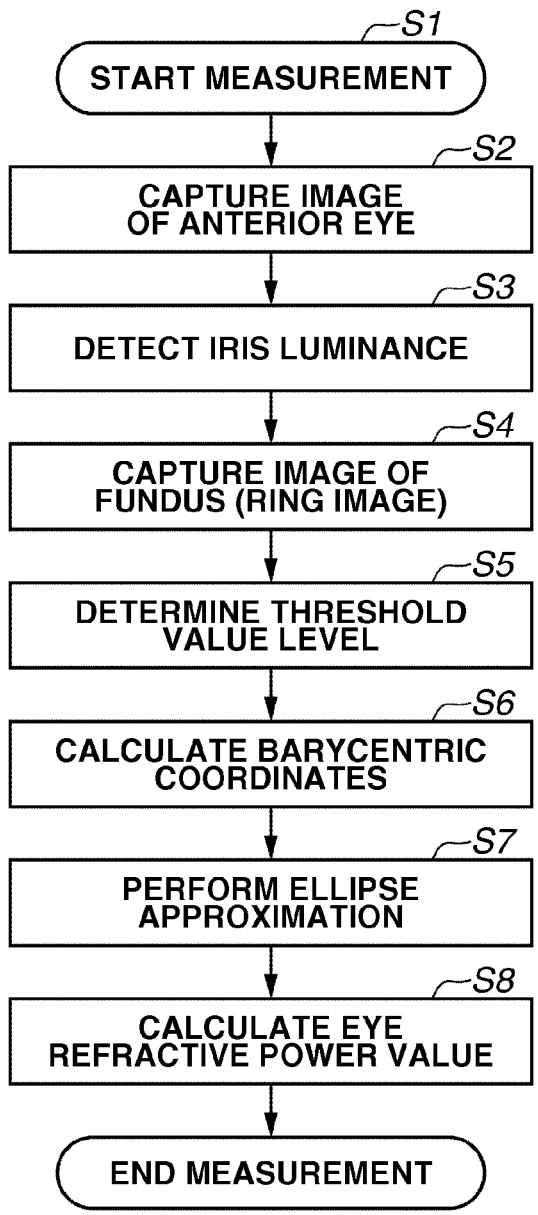

OPHTHALMOLOGIC APPARATUS, OPHTHALMOLOGIC CONTROL METHOD, AND PROGRAM

BACKGROUND OF THE INVENTION

1. Field of the Invention

The present invention relates to an ophthalmologic apparatus, an ophthalmologic control method, and a program for acquiring unique information (for example, an eye refractive power and a fundus image) of a subject's eye.

2. Description of the Related Art

As an ophthalmologic apparatus configured to acquire unique information of a subject's eye, for example, Japanese Patent No. 4545871 discusses a dioptometer for measuring a refractive power of an eye. This dioptometer projects an index light flux to a fundus of a subject's eye, and captures a ring image from the fundus by an imaging unit via a ring diaphragm prism. The dioptometer acquires a shape of the ring image based on an output of the imaging unit via a threshold value as a predetermined parameter, and calculates an eye refractive power value based on the acquired shape. For this purpose, Japanese Patent No. 4545871 discusses scanning the ring image from a center in a horizontal direction, a vertical direction, and a diagonal direction to acquire positions of barycentric coordinates, performing elliptical approximation based on the positions of barycentric coordinates in all directions, and calculating the eye refractive power value.

SUMMARY OF THE INVENTION

The present invention is directed to acquiring correct unique information of a subject's eye while reducing a load applied to a subject by reducing a time taken to acquire the unique information.

According to an aspect of the present invention, an ophthalmologic apparatus includes a projection unit configured to project a light flux to a subject's eye, an imaging optical system configured to form an image of the light flux reflected by the subject's eye or an image of the subject's eye on an imaging plane, an imaging unit provided on the imaging plane of the imaging optical system, a determination unit configured to determine a parameter regarding the imaging unit or the projection unit for acquiring unique information of the subject's eye based on a physical property of the subject's eye, and an acquisition unit configured to acquire the unique information based on the image of the light flux or the image of the subject's eye captured by the imaging unit with use of the determined parameter.

According to another aspect of the present invention, an ophthalmologic control method includes projecting a light flux to a subject's eye, capturing, by an imaging unit provided on an imaging plane, an image of the light flux reflected by a predetermined portion of the subject's eye or an image of the predetermine portion via an imaging optical system, determining, by a determination unit, a parameter for acquiring unique information of the subject's eye based on a physical property of the subject's eye, and acquiring the unique information based on outputs of the imaging unit and the determination unit.

Further features of the present invention will become apparent from the following description of exemplary embodiments with reference to the attached drawings.

BRIEF DESCRIPTION OF THE DRAWINGS

FIG. 9 is a flowchart according to an exemplary embodiment of the present invention.

DESCRIPTION OF THE EMBODIMENTS

Figure 1A:
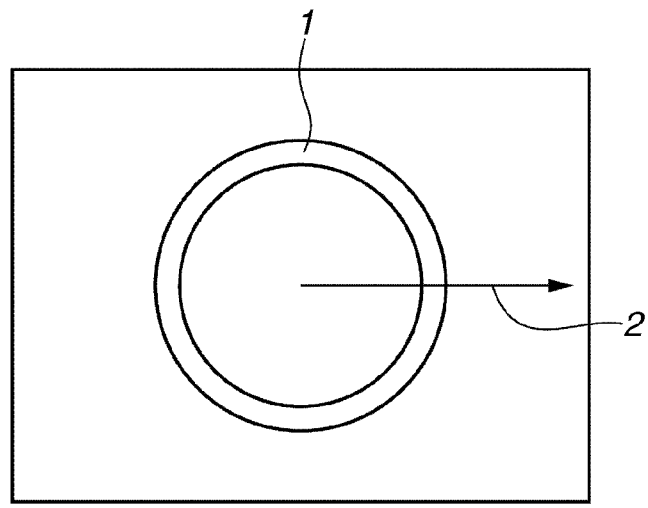
FIG. 1A illustrates a ring image that is an image reflected by a fundus.

When an eye refractive power value is calculated from a shape of a ring image based on an output of an imaging unit via a threshold value as a predetermined parameter, there is such a problem that a difference in fundus scattering rate among races due to a pigment of a fundus leads to a difference in luminance distribution of a captured ring image. More specifically, FIG. 1A illustrates a captured ring image 1, and FIGS. 1B and 1C each illustrate luminance distribution when this ring image 1 is scanned as indicated by an arrow 2.

Figure 1B:
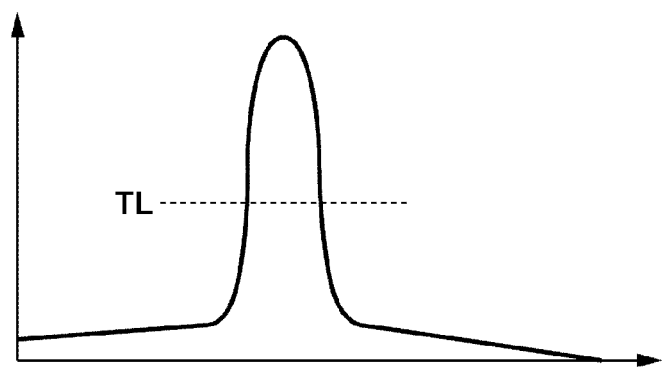
FIG. 1B illustrates an example of luminance distribution of a ring image of a Japanese person.
Figure 1C:
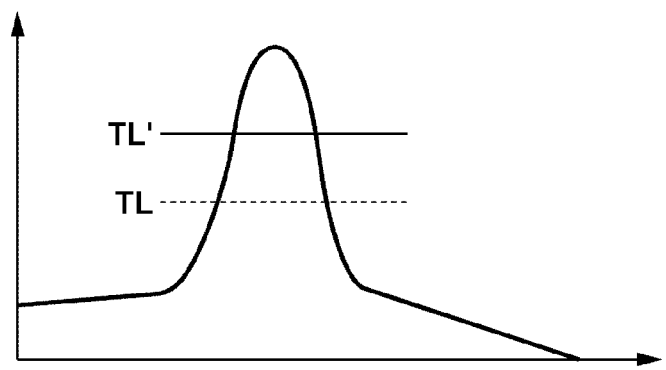
FIG. 1C illustrates an example of luminance distribution of a ring image of a Westerner.

FIG. 1B illustrates luminance distribution of an ordinary Japanese person, and FIG. 1C illustrates luminance distribution of an ordinary Westerner. Generally, the fundus scattering rate of a Westerner is higher than that of a Japanese person, whereby luminance distribution thereof is overall high. Further, in the luminance distribution of a Westerner, a center of the distribution tends to more scatter than ends of the distribution compared to the luminance distribution of a Japanese person, whereby the luminance distribution of a ring image tends to have broken left-right symmetry. Therefore, there is such a problem that, assuming that TL for a Japanese person is the threshold value level as the predetermined parameter for calculating barycentric coordinates, barycentric coordinates in FIG. 1C shift to the inner side of the ring image, making calculation of a correct measured value impossible.

According to an exemplary embodiment of the present invention, it is possible to determine a parameter regarding an imaging unit or a projection unit for acquiring unique information of a subject's eye based on a physical property of the subject's eye. As a result, it is possible to acquire correct unique information while reducing a load applied to the subject by reducing a time taken to acquire the unique information.

(Dioptometer)

Figure 2:
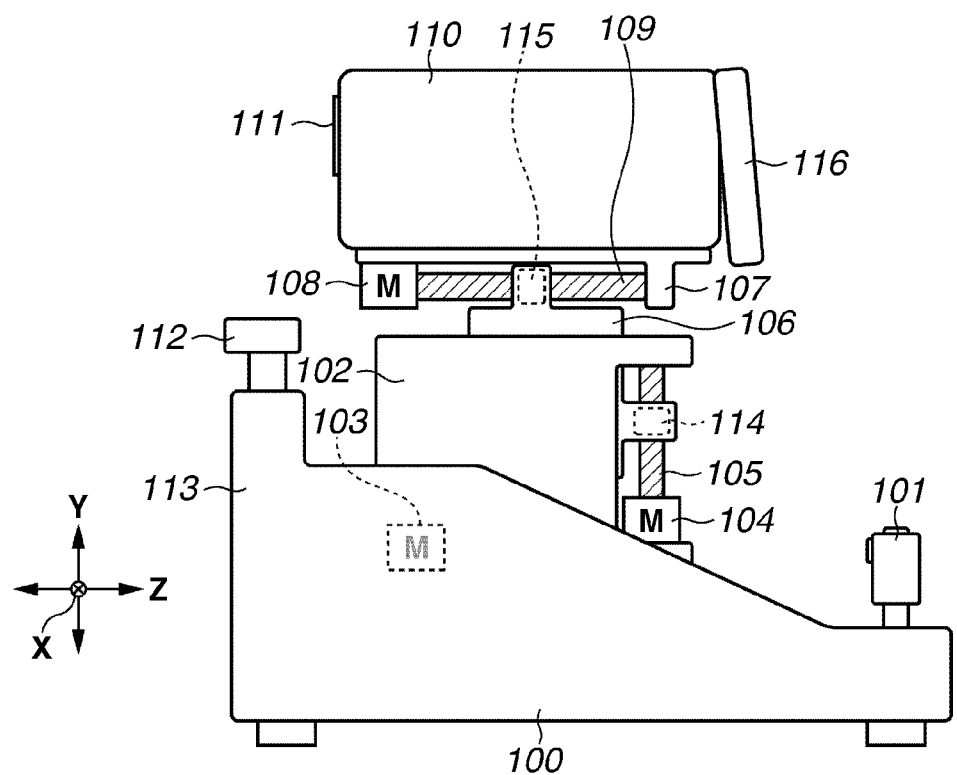
FIG. 2 illustrates an outline of a configuration of a dioptometer according to an exemplary embodiment of the present invention.

FIG. 2 illustrates an outline of a configuration of a dioptometer that measures eye refractive power information, as an ophthalmologic apparatus according to a first exemplary embodiment of the present invention. A frame 102 is movable relative to a base 100 in a left-right direction (hereinafter referred to as an X-axis direction). A driving mechanism in the X-axis direction includes an X-axis driving motor 103 fixed on the base 100, a feed screw (not illustrated) coupled to a motor output shaft, and a nut (not illustrated) movable along the feed screw in the X-axis direction and fixed to the frame 102. The frame 102 moves in the X-axis direction by a rotation of the motor 103 via the feed screw and the nut.

A frame 106 is movable relative to the frame 102 in a vertical direction (hereinafter referred to as a Y-axis direction). A driving mechanism in the Y-axis direction includes a Y-axis driving motor 104 fixed on the frame 102, a feed screw 105 coupled to a motor output shaft, and a nut 114 movable along the feed screw 105 in the Y-axis direction and fixed to the frame 106. The frame 106 moves in the Y-axis direction by a rotation of the motor 104 via the feed screw 105 and the nut 114.

A frame 107 is movable relative to the frame 106 in a front-back direction (hereinafter referred to as a Z-axis direction). A driving mechanism in the Z-axis direction includes a Z-axis driving motor 108 fixed on the frame 107, a feed screw 109 coupled to a motor output shaft, and a nut 115 movable along the feed screw 109 in the Z-axis direction and fixed to the frame 106. The frame 107 moves in the Z-axis direction by a rotation of the motor 108 via the feed screw 109 and the nut 115. A measurement unit 110 for performing measurement is fixed on the frame 107. The measurement unit 110 functions as an acquisition unit that acquires an eye refractive power, which is one of unique information pieces of a subject's eye.

A light source (not illustrated) for performing alignment, and a light source unit 111 for measuring a corneal curvature are disposed at an end of the measurement unit 110 on a subject side. Further, a joystick 101, which is an operation member for positioning the measurement unit 110 relative to a subject's eye E illustrated in FIG. 3, is disposed at the frame 100, and the position of the measurement unit 110 can be adjusted by tilting the joystick 101 to perform measurement.

When an eye refractive power is measured, a subject places his/her chin on a chin rest 112 and presses his/her forehead against a forehead rest portion of a face rest frame (not illustrated) fixed to the frame 100, whereby the position of the subject's eye E can be fixed. Further, the chin rest 112 can be adjusted in the Y-axis direction by a chin rest driving mechanism (chin rest motor) 113 according to a size of a subject's face. A liquid crystal display (LCD) monitor 116, which is a display member for observing the subject's eye E, is disposed at an end of the measurement unit 110 on an operator side, and can display a measurement result and the like.

(Eye Refractive Power Measurement Unit)

Figure 3:
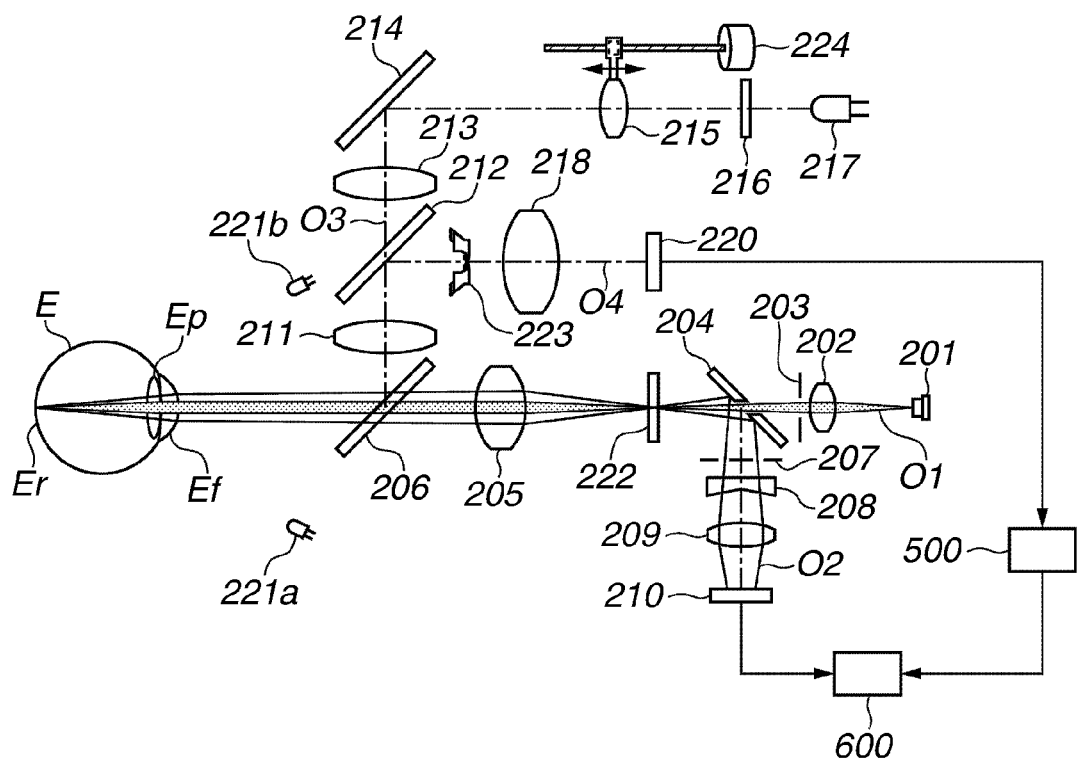
FIG. 3 is an arrangement diagram mainly illustrating an optical system of a measurement unit according to an exemplary embodiment of the present invention.

FIG. 3 is an arrangement diagram mainly illustrating an optical system inside the measurement unit 110. A lens 202 as a projection unit, and a diaphragm 203 substantially conjugate to a pupil Ep of the subject's eye E are disposed in this order on an optical path O1 from an eye refractive power measurement light source 201, which is used for projecting light having a wavelength of 880 nm to a fundus as a predetermined portion of the subject's eye E, to the subject's eye E. Further, a perforated mirror 204, a lens 205 as a projection unit, and a dichroic mirror 206 are disposed in this order. The dichroic mirror 206 reflects whole infrared light and visible light having a wavelength less than 880 nm from the subject's eye E side, and partly reflects a light flux having a wavelength of 880 nm or longer from the subject's eye E side.

A diaphragm 207, a light flux spectral prism 208, a lens 209, and an image sensor 210 are arranged in this order on an optical path O2 indicating a direction in which the perforated mirror 204 reflects light. The diaphragm 207 is substantially conjugate to the pupil Ep and includes an annular slit.

The above-described optical system is used for measurement of an eye refractive power. A light flux emitted from the measurement light source 201 is primarily imaged by the lens 202 before the lens 205 while being narrowed by the diaphragm 203, is transmitted through the lens 205 and the dichroic mirror 206, and is projected to an eye center of the subject's eye E.

The projected light flux is reflected by a fundus, and an image of the reflected light flux is formed on an imaging unit positioned on an imaging plane via an imaging optical system. More specifically, the light reflected by the fundus is transmitted through the center of the eye to be introduced into the lens 205 again, and the introduced light flux is reflected around the perforated mirror 204 after being transmitted through the lens 205. Then, the reflected light flux is separated by pupil separation by the diaphragm 207 substantially conjugate to the pupil Ep of the subject's eye E and the light flux spectral prism 208, and is projected on a light receiving surface of the image sensor 210 as a ring image.

If the subject's eye E is an emmetropic eye, this ring image has a predetermined circular form. If the subject's eye E is a myopic eye, the ring image is projected as a smaller circle compared to the emmetropic eye. If the subject's eye E is a hyperopic eye, the ring image is projected as a larger circle compared to the emmetropic eye. If the subject's eye E is an astigmatic eye, the ring image has an elliptical form, and an angle defined by a horizontal axis and the elliptical form is an astigmatism axis angle. An eye refractive power is calculated based on a coefficient of this ellipse.

On the other hand, a fixation target projection optical system, and an alignment light receiving optical system used for both observation of an anterior eye of the subject's eye E and alignment detection are disposed in a direction in which the dichroic mirror 206 reflects light. A lens 211, a dichroic mirror 212, a lens 213, a reflecting mirror 214, a lens 215, a fixation target 216, and a fixation target illumination light source 217 are arranged in this order on an optical path O3 of the fixation target projection optical system.

When visual fixation is guided, a projection light flux of the lighted fixation target illumination light source 217 illuminates the fixation target 216 from behind, and is projected on the fundus Er of the subject's eye E via the lens 215, the reflecting mirror 214, the lens 213, the dichroic mirror 212, and the lens 211. The lens 215 is configured to be movable in an optical axis direction by a fixation target guiding motor 224 to guide a diopter of the subject's eye E to realize a fogged state.

Further, an alignment prism diaphragm 223 configured to be inserted and removed by an alignment prism diaphragm insertion/removable solenoid (not illustrated), a lens 218, and an image sensor 220 are arranged in this order on an optical path O4 indicating a direction in which the dichroic mirror 212 reflects light. By inserting and removing the alignment prism diaphragm 223, it is possible to perform alignment when the alignment prism diaphragm 223 is positioned on the optical path O4, and perform an anterior eye observation or transillumination observation when the alignment prism diaphragm 223 is retracted from the optical path O4.

Figure 4:
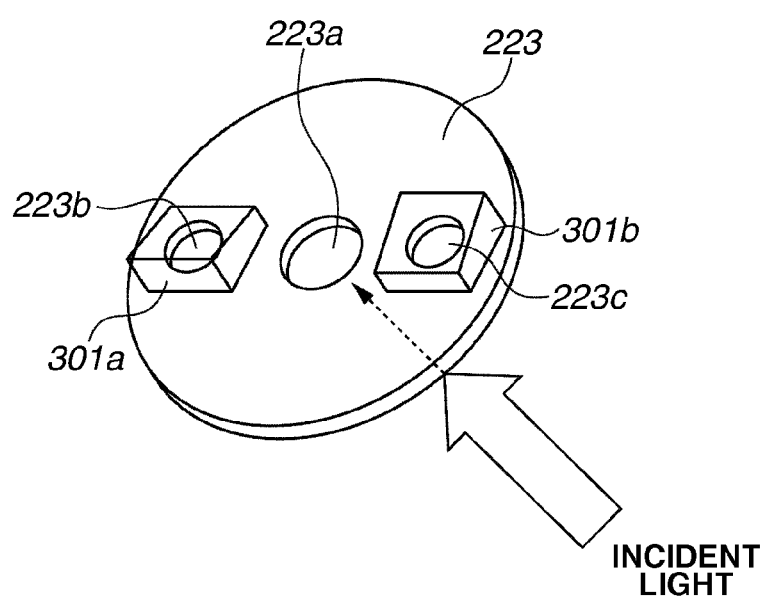
FIG. 4 is a perspective view illustrating an alignment prism diaphragm according to an exemplary embodiment of the present invention.
Figure 5:
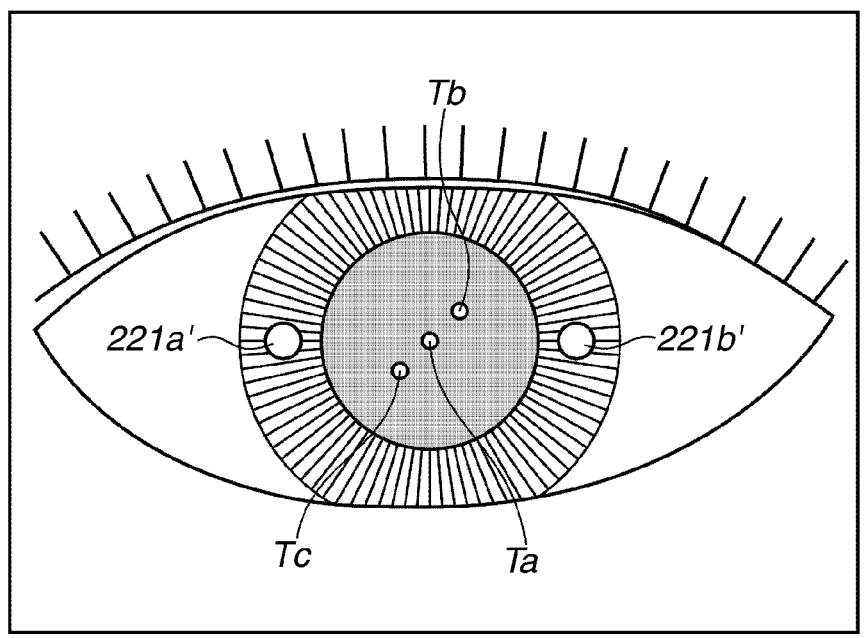
FIG. 5 illustrates an image of an anterior eye at the time of automatic alignment according to an exemplary embodiment of the present invention.

FIG. 4 illustrates a shape of the alignment prism diaphragm 223. Three openings 223a, 223b, and 223c are formed on a disk-like diaphragm plate. Alignment prisms 301a and 301b, which allow transmission of only a light flux having a wavelength around 880 nm, are attached to the openings 223b and 223c at both sides on a surface of the diaphragm plate that faces the dichroic mirror 212.

Anterior eye illumination light sources 221a and 221b, which have a wavelength around 780 nm, are disposed diagonally in front of the anterior eye of the subject's eye E. An image of the anterior eye of the subject's eye E illuminated with these anterior eye illumination light sources 221a and 221b is formed on a light receiving sensor surface of the image sensor 220 via the dichroic mirror 206, the lens 211, the dichroic mirror 212, and the central opening 223a of the alignment prism diaphragm 223.

A light source for alignment detection is the measurement light source 201, which is also used to measure an eye refractive power. At the time of alignment, a translucent diffusion plate 222 is inserted into the optical path O1 by a diffusion plate insertion/removal solenoid (not illustrated). A position where the diffusion plate 222 is inserted substantially corresponds to a position of primary image forming by the projection lens 202 of the measurement light source 201, and a focal position of the lens 205. As a result, an image of the measurement light source 201 is formed on the diffusion plate 222 first, and this works as a secondary light source and is projected from the lens 205 toward the subject's eye E as a wide collimated light flux.

This collimated light flux is reflected by a cornea Ef of the subject's eye E to form a luminescent spot image. Then, the light flux is partially reflected by the dichroic mirror 206 again, and is reflected by the dichroic mirror 212 via the lens 211. Further, the light flux is transmitted through the openings 223b and 223c and the alignment prisms 301a and 301b of the alignment prism diaphragm 223, and is converged by the lens 218 to be imaged on the image sensor 220.

The central opening 223a of the alignment prism diaphragm 223 allows transmission of a light flux having a wavelength of 780 nm or longer emitted from the anterior eye illumination light sources 221a and 221b. Therefore, a light flux reflected by the anterior eye illuminated with the anterior eye illumination light sources 221a and 221b is transmitted along an observation optical system, in a similar manner to the route of the light flux reflected by the cornea Ef, and is imaged on the image sensor 220 by the imaging lens 218 via the opening 223a of the alignment prism diaphragm 223.

Figure 6A:
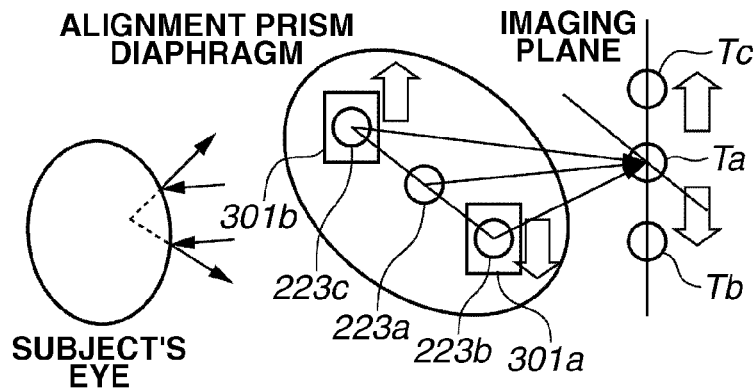
FIG. 6A illustrates a state in which the measurement unit is aligned with a subject's eye in a front-back direction using the alignment prism diaphragm.
Figure 6B:
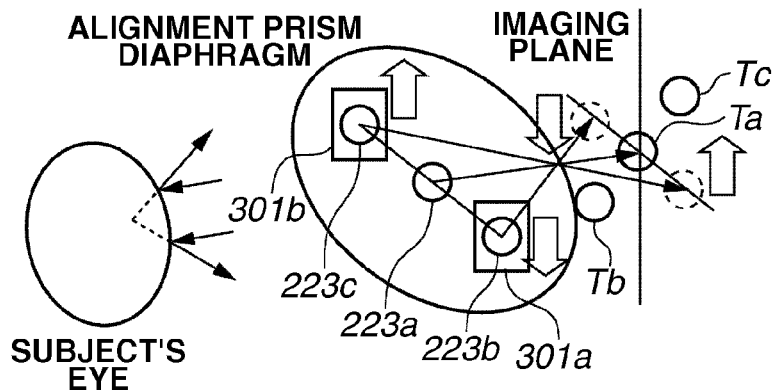
FIG. 6B illustrates a state in which the measurement unit is located too far away from the subject's eye.
Figure 6C:
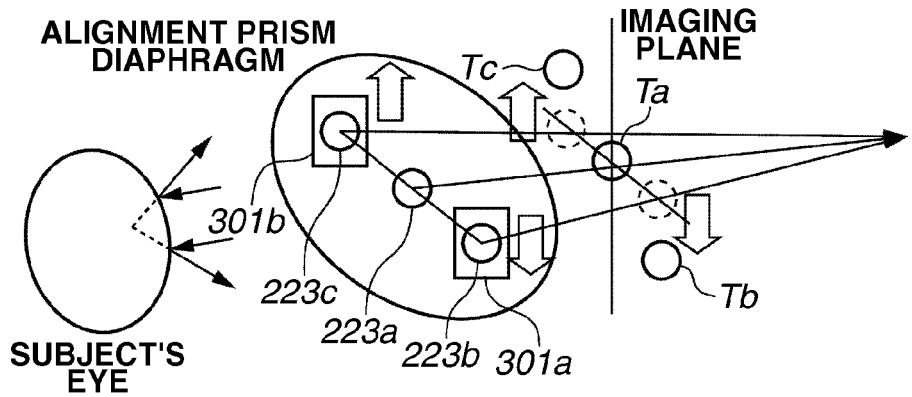
FIG. 6C illustrates a state in which the measurement unit is located too close to the subject's eye.

Further, as illustrated in FIGS. 6A, 6B, and 6C, the light flux transmitted through the alignment prism 301a is refracted downward, and the light flux transmitted through the alignment prism 301b is refracted upward. Alignment of the subject's eye E can be performed based on a positional relationship between these light fluxes via the diaphragm.

As illustrated in FIG. 3, an output of the image sensor 220 is input into a detection unit 500 configured to detect a luminance or a hue of an iris of the subject's eye E. Outputs of the detection unit 500 and the image sensor 210 are input into a unique information acquisition unit 600. The image sensor 220 and the detection unit 500 function as a unit that determines a parameter for acquiring the unique information of the subject's eye E together with a system control unit 401.

(System Control Unit)

Figure 7:
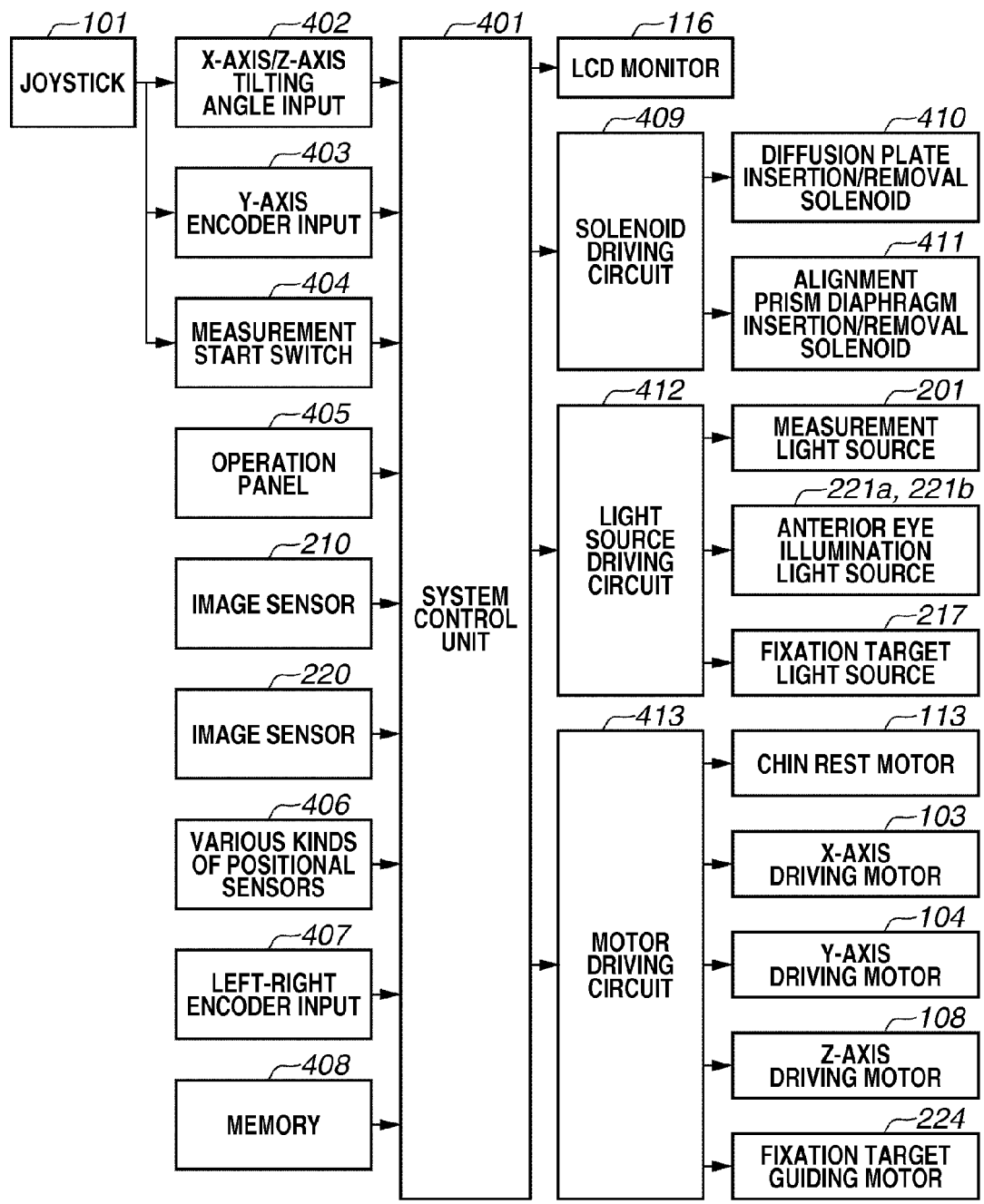
FIG. 7 is a block diagram illustrating a system of the dioptometer according to an exemplary embodiment of the present invention.

FIG. 7 is a system block diagram. The system control unit 401, which controls the whole system, includes a program storage unit, a data storage unit that stores data for correcting an eye refractive power value, an input/output control unit that controls an input into and an output from various kinds of devices, and a calculation processing unit that calculates data acquired from the various kinds of devices.

The joystick 101, which positions the measurement unit 110 relative to the subject's eye E and starts measurement, is connected to the system control unit 401. Further, an X-axis/Z-axis tilting angle input 402 when the joystick 101 is tilted in the front-back direction and the left-right direction, respectively, a Y-axis encoder input 403 when the joystick 101 is rotated, and a measurement start switch 404 when a measurement start button is pressed are connected to the system control unit 401. Further, a print button, a chin rest vertically moving button, and the like are disposed on an operation panel 405 of the base 100 illustrated in FIG. 2, and a signal is transmitted to the system control unit 401 when the button is input.

The image of the anterior eye of the subject's eye E captured by the image sensor 220 is stored in a memory 408. A pupil image and a cornea reflection image of the subject's eye E are extracted from the image stored in the memory 408, and alignment detection is performed. Further, the image of the anterior eye of the subject's eye E captured by the image sensor 220 is combined with character data and graphic data, and the image of the anterior eye, a measured value, and the like are displayed on the LCD monitor 116. A ring image for calculating an eye refractive power, which is captured by the image sensor 210, is stored in the memory 408.

The diffusion plate insertion/removal solenoid 410 and the alignment prism diaphragm insertion/removal solenoid 411 are driven and controlled based on an instruction from the system control unit 401 via a solenoid driving circuit 409. Further, the X-axis driving motor 103, the Y-axis driving motor 104, the Z-axis driving motor 108, the chin rest motor 113, and the fixation target guiding motor 224 are driven based on an instruction from the system control unit 401 via a motor driving circuit 413. The measurement light source 201, the anterior eye illumination light sources 221a and 221b, and the fixation target light source 217 are controlled to be turned on, turned off, and change a light amount based on an instruction from the system control circuit 401 via a light source driving circuit 412.

(Description of Operation)

An operation of the apparatus configured in the above-described manner will be described. As illustrated in FIGS. 5, 6A, 6B, and 6C, at the time of alignment, an image of a cornea luminescent spot formed by the cornea Ef is captured by the image sensor 220 as index images Ta, Tb, and Tc. More specifically, light fluxes divided by the openings 223a, 223b, and 223c, and the prisms 301a and 301b of the alignment prism diaphragm 223 are imaged on the image sensor 220 as the index images Ta, Tb, and Tc. Further, luminescent spot images 221a' and 221b' of the anterior eye illumination light sources 221a and 221b are captured by the image sensor 220 together with an image of the anterior eye of the subject's eye E illuminated with the anterior eye illumination light sources 221a and 221b.

After the three luminescent points Ta, Tb, and Tc are detected, the system control unit 401 controls the motor driving circuit 413 to drive the measurement unit 110 in the vertical direction and the left-right direction in such a manner that the central luminescent point Ta is aligned in the central direction. Next, the system control unit 401 drives the measurement unit 110 in the front-back direction in such a manner that the luminescent points Tb and Tc are vertically aligned with the luminescent point Ta. The alignment is completed in such a state that the three cornea luminescent points Ta, Tb, and Tc are vertically aligned to form a single line as illustrated in FIG. 6A. When the alignment is in a faulty state in the Z-axis direction (the front-back direction), the luminescent points Ta, Tb, and Tc are set in a positional relationship illustrated in FIG. 6B with the measurement unit 110 positioned too far away from the subject's eye E, and the luminescent points Ta, Tb, and Tc are set in a positional relationship illustrated in FIG. 6C with the measurement unit 110 positioned too close to the subject's eye E.

The system control unit 401 causes the diffusion plate 222 inserted in the optical path O1 for automatic alignment to be retracted from the optical path O1 to measure an eye refractive power. A light amount of the measurement light source 201 is adjusted, and a measurement light flux is projected on the fundus Er of the subject's eye E. Reflected light from the fundus is transmitted along the optical path O2, and is received by the image sensor 210. A captured fundus image is projected as a ring shape by the ring diaphragm 207 due to a refractive power of the subject's eye E.

This ring image is stored in the memory 408. The system control unit 401 calculates barycentric coordinates of the ring image stored in the memory 408, and calculates an equation of an ellipse. The system control unit 401 calculates lengths of a major axis and a minor axis of the acquired ellipse and an inclination of the major axis of the acquired ellipse, and calculates an eye refractive power value in preliminary measurement of the subject's eye E. Whether the subject's eye E is a myopic eye or a hyperopic eye is determined from this preliminary measurement.

The system control unit 401 drives the fixation target guiding motor 224 to a position corresponding to the acquired eye refractive power value via the motor driving circuit 413 to move the lens 215, thereby providing the fixation target 216 to the subject's eye E at a refractivity corresponding to a refractivity of the subject's eye E. After that, the system control unit 401 moves the lens 215 away by a predetermined amount to fog the fixation target 216, and turns on the measurement light source 201 again to measure the eye refractive power. In this manner, the system control unit 401 repeats the measurement of the eye refractive power, the fogging of the fixation target 216, and the measurement of the eye refractive power, by which it is possible to acquire a final measurement value based on which the eye refractive power is stabilized.

Figure 8A:
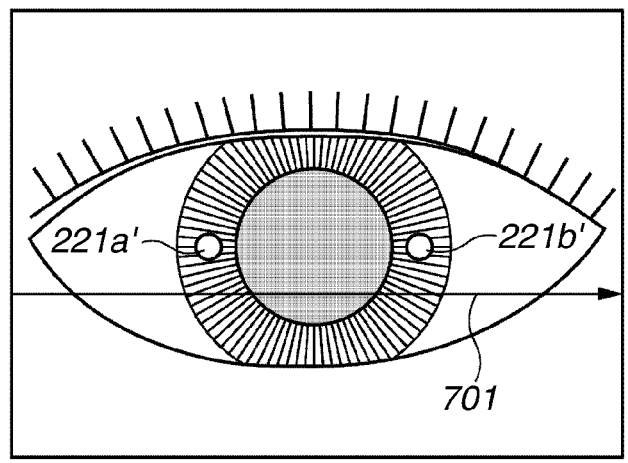
FIG. 8A illustrates an image of an anterior eye when an iris luminance is detected.
Figure 8B:
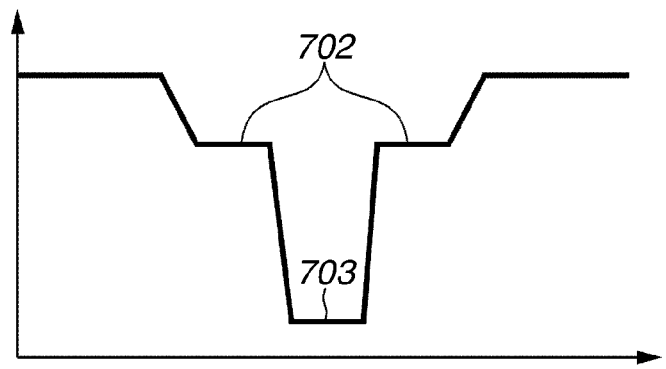
FIG. 8B illustrates an example of luminance distribution of an anterior eye image of a Japanese person.
Figure 8C:
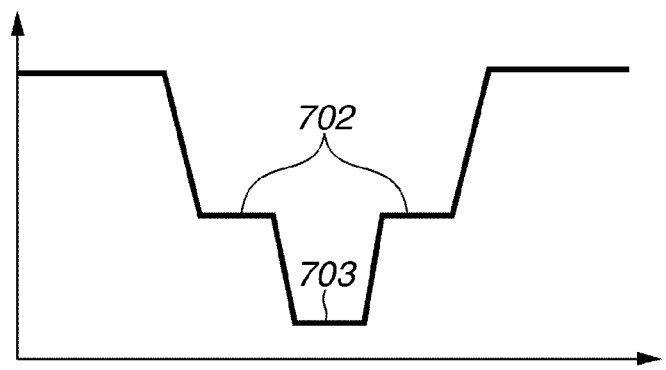
FIG. 8C illustrates an example of luminance distribution of an anterior eye image of a Westerner.

FIG. 8A illustrates an image of the anterior eye captured after completion of the alignment with the measurement light source 201 turned off. FIGS. 8B and 8C each illustrate luminance distribution when the image is scanned as indicated by an arrow 701. FIG. 8B illustrates luminance distribution of a Japanese person, and FIG. 8C illustrates luminance distribution of a Westerner, both of which include an iris 702 and a pupil portion 703. If the color of the iris is brown or a similar color like Japanese, the reflected light from the iris contains large amounts of reflection components of the red (R) color and the green (G) color, whereby the iris has a high luminance when being illuminated with the anterior eye illumination light sources 221a and 221b of near-infrared light.

On the other hand, if the color of the iris is blue or a similar color like Westerners, the reflected light from the iris contains large amounts of reflection components of the G color and the blue (B) color but contains a small amount of the reflection component of the R color, whereby the iris has a low luminance when being illuminated with near-infrared light. A race can be determined by detecting a luminance of an iris.

The present exemplary embodiment determines the threshold value as the predetermined parameter according to a race as will be described below, assuming that a level of a fundus scattering rate as a physical property of a subject's eye varies depending on a race, and there is such a correlation that the fundus scattering rate is high for Westerners whose iris is blue.

(Flowchart)

FIG. 9 is a flowchart for calculating an eye refractive power value. The calculation flow will be described. In step S1, an operator instructs a subject to place his/her chin on the chin rest 112, and adjusts it in the Y-axis direction by the chin rest driving mechanism 113 so as to achieve a predetermined height of the subject's eye E. The operator operates the joystick 101 until the subject's eye E reaches a position allowing a display of a cornea reflection image of the subject's eye E displayed on the LCD monitor 116, and then presses the measurement start button. Upon pressing of the measurement start button, the automatic alignment starts. A cornea reflection image is extracted from an anterior eye image of the subject's eye E stored in the memory 408, and alignment is performed according to the above-described alignment method.

In step S2, after completion of the alignment, the system control unit 401 turns off the measurement light source 201, turns on the anterior eye illumination light sources 221a and 221b so that they emit a predetermined light amount, captures an anterior eye image, and stores the captured image into the memory 408. In step S3, as illustrated in FIG. 8A, the system control unit 401 acquires luminance distribution along a horizontal one line that does not contain the luminescent spot images 221a' and 221b' of the anterior eye illumination light sources 221a and 221b, from the anterior eye image stored in the memory 408.

The system control unit 401 scans the image from the pupil portion at the center, detects a portion where the luminance level largely increases as an inner edge of the iris, scans the image from a scleral portion at an outer side, and detects a portion where the luminance level largely reduces as an outer edge of the iris. The system control unit 401 determines that a portion between the outer edge and the inner edge of the iris is an iris portion, and sets an average luminance in the iris portion as an iris luminance. In step S4, the system control unit 401 stores a fundus ring image received by the image sensor 210 into the memory 408.

In step S5, the system control unit 401 determines a threshold value level for calculating barycentric coordinates of the ring image based on the iris luminance acquired in step S3. If the iris luminance is low, the system control unit 401 determines that this iris belongs to a Westerner, whose iris is generally blue (a fundus scattering rate is higher than a reference scattering rate), and therefore sets the threshold value level to a higher value than a reference threshold value. On the other hand, if the iris luminance is high, the system control unit 401 determines that this iris belongs to a Japanese person, and therefore sets the threshold value level to a low value.

According to the conventional technique, there is such a problem that, when the system control unit 401 determines that the iris belongs to a Japanese person, setting the threshold value level to a threshold value level TL' for Westerners illustrated in FIG. 1C leads to a variation in a measured value because this setting results in a reduction in a data amount for calculating barycentric coordinates for Japanese. Therefore, when a correct measured value cannot be acquired under such a circumstance, the measurement has to be performed several times while changing the threshold value level by trial and error until a correct measured value can be calculated without a variation in each measured value, which increases a time taken for the measurement.

To avoid this problem, in the present exemplary embodiment, the system control unit 401, which functions as a unit configured to determine a parameter for acquiring unique information of a subject's eye, determines the threshold value as the predetermined parameter according to a race.

In step S6, the system control unit 401 scans the ring image in the horizontal, vertical, and diagonal directions to calculate barycentric positions, in a similar manner to the method discussed in Japanese Patent No. 4545871, with use of the threshold value level determined in step S5. In step S7, the system control unit 401 performs elliptical approximation by the least-square method with use of the barycentric coordinates calculated in step S6 to acquire an equation of an ellipse. In step S8, the system control unit 401 calculates lengths of major and minor axes and an inclination of the major axis of the ellipse acquired in step S7, and calculates an eye refractive power value of the subject's eye E.

In step S2 in the above-described measurement flow, the illumination light amount is fixed, but the iris luminance may be calculated based on a relationship between the illumination light amount and a detected luminance of the iris portion. Further, in step S5, the system control unit 401 uses two types of levels for Japanese and Westerners as the threshold value levels. However, the system control unit 401 may use three types or more of threshold value levels based on a correlation function between the iris luminance and the threshold value level. Further, the system control unit 401 determines only the threshold value level at the time of calculation of the barycentric coordinates as the parameter, based on the iris luminance. However, because reflection and scattering of a fundus varies depending on a race, the system control unit 401 may determine an illumination light amount parameter, which is used to adjust the illumination light amount of the measurement light source 201 at the time of capturing a fundus ring image, based on the iris luminance.

According to the above-described exemplary embodiment, the system control unit 401 captures the anterior eye image by near-infrared light to acquire the iris luminance information. However, the system control unit 401 may capture the anterior eye image by visible light, and determine the threshold value level at the time of calculation of the barycentric coordinates as the parameter, based on hue information of the iris.

The first exemplary embodiment relates to the apparatus for measuring an eye refractive power. A second exemplary embodiment relates to a fundus camera, and determines a color conversion parameter as a fundus imaging parameter, based on iris luminance information.

When a color fundus image is captured, Westerners have a background color (a color of a whole fundus area) different from Japanese, based on the fact that the level of the fundus scattering rate as a physical property of a subject's eye varies depending on a race, and there is such a correlation that the fundus scattering rate is high for Westerners whose iris is blue. The present exemplary embodiment determines the color conversion parameter as the fundus imaging parameter according to a race so as to realize a constant background color (a color of a whole fundus area) regardless of a race (to maintain a background color which an operator is familiar with), thereby facilitating diagnosis of a fundus portion.

When a subject is determined as a Westerner, the present exemplary embodiment performs color conversion in such a manner that the background color (the color of the whole fundus area) becomes the same as or similar to the background color (the color of the whole fundus area) of Japanese. Determining a subject as a Westerner includes not only determining a subject as a Westerner based on an output of the anterior eye imaging unit, but also an operator's recognizing that a subject is a Westerner and manually inputting it by an input switch.

Conversely, the present exemplary embodiment can be even configured so as to perform color conversion in such a manner that, when a subject is determined as a Japanese person, the background color (the color of the whole fundus area) becomes the same as or similar to the background color (the color of the whole fundus area) of Westerners. This configuration is useful when an operator is a Westerner.

According to the present exemplary embodiment, it is possible to shoot a fundus photo with little difference among races by setting the color conversion parameter according to a race at the time of shooting a color image despite the fact that a pigment of a fundus varies depending on a race. By shooting a fundus in this manner, it is possible to shoot a fundus photo as fundus imaging information advantageous to an operator in a short time.

The above-described first exemplary embodiment determines the threshold value parameter according to a race, assuming that the level of the fundus scattering rate as a physical property of a subject's eye varies depending on a race and there is such a correlation that the fundus scattering rate is high for Westerners whose iris is blue. Further, the second exemplary embodiment determines the color conversion parameter according to a race, assuming that the fundus scattering rate is high for Westerners whose iris is blue and Westerners have a different background color (the color of the whole fundus area) from Japanese.

A third exemplary embodiment relates to a dioptometer, and determines the illumination light amount parameter, which is used to adjust the illumination light amount, according to a diopter as a physical property of a subject's eye (whether the eye is in a myopic state or a hyperopic state), independently of a race of a subject. The myopic state means a refractive state in which a collimated light ray transmitted from infinity is imaged in front of a retina in an eye in an unadjusted state, and the hyperopic state means a refractive state in which a collimated light ray transmitted from infinity is imaged behind a retina in an eye in an unadjusted state.

If a subject's eye is a myopic eye, a fundus position is far away from the ophthalmologic apparatus side, leading to a reduction in the imaging light amount compared to a hyperopic eye, whereby it is desirable to increase the illumination light amount to compensate for this reduction. Therefore, the present exemplary embodiment determines the illumination light amount parameter so as to increase the illumination light amount to compensate for the reduction in the imaging light amount for a myopic eye according to a result of preliminary measurement of an eye refractive power of a subject's eye.

(Ophthalmologic Control Program)

The embodiments of the present invention can be also realized by performing the following processing as an ophthalmologic control program in association with the ophthalmologic control method based on the above-described flowchart. This processing is processing for supplying software or a program for realizing functions of the above-described exemplary embodiments to a system or an apparatus via a network or any of various kinds of storage media, and causing a computer, a central processing unit (CPU), or a micro processing unit (MPU) of the system or the apparatus to read out and execute the program.

Modification Example 1

The above-described exemplary embodiments have been described based on the dioptometer and the fundus camera. However, the present invention is not limited thereto. For example, the present invention can be employed for an ophthalmologic apparatus (an ophthalmologic optical coherence tomography (OCT) apparatus) that scans and images a subject's eye and acquires a tomographic image of a fundus based on optical interference of near-infrared laser, and a scanning laser ophthalmoscope (ophthalmologic scanning laser ophthalmoscope (SLO) apparatus) that acquires a fundus image using a confocal point. Further, the present invention can be also employed for a transillumination image observation apparatus, a blood flowmeter that measures a blood flow amount in a blood vessel at a fundus, and the like.

Modification Example 2

Regarding the alignment prism diaphragm 223, the opening and the prisms are arranged along the optical path in this order. However, conversely, the prisms and the opening may be arranged in this order.

Modification Example 3

The above-described exemplary embodiments have been described based on the refractometer and the fundus camera that capture an image of a light flux reflected by a fundus as a predetermined portion of a subject's eye, and acquires unique information of the subject's eye. However, the present invention is not limited thereto. In other words, the present invention can be also employed for a keratometer that captures an image of a light flux reflected by a cornea as a predetermined portion of a subject's eye and acquires unique information (cornea shape information) of the subject's eye. In this case, the keratometer determines whether a ratio of noise light transmitted through the cornea and scattered by an iris relative to measurement light (signal light) reflected by the cornea is high or low as a physical property of the subject's eye by detecting a diameter of a pupil.

Then, if the diameter of the pupil is small, the keratometer determines that the ratio of the noise light scattered by the iris is high, and measures a shape of the cornea while reducing a light amount of a cornea shape measurement light source as the parameter for acquiring the unique information of the subject's eye.

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-230783 filed Oct. 18, 2012, which is hereby incorporated by reference herein in its entirety.

What is claimed is:

1. An ophthalmologic apparatus comprising:
an optical system configured to capture an image of a subject's eye by using an imaging unit and returned light from the subject's eye irradiated with illumination light;
a determination unit configured to determine a parameter for acquiring unique information of the subject's eye based on a physical property of the subject's eye; and
an acquisition unit configured to acquire the unique information based on the determined parameter and an output of the imaging unit.

2. The ophthalmologic apparatus according to claim 1, wherein the acquisition unit acquires eye refractive power information by calculating a barycentric position of the captured image with use of the determined parameter.

3. The ophthalmologic apparatus according to claim 1, wherein the acquisition unit acquires the captured image of the subject's eye on which color conversion is performed with use of the determined parameter.

4. The ophthalmologic apparatus according to claim 3, wherein the image of the subject's eye is a fundus image.

5. The ophthalmologic apparatus according to claim 1, wherein the acquisition unit acquires refractive power information while adjusting an amount of the illumination light with use of the determined parameter.

6. The ophthalmologic apparatus according to claim 1, wherein the physical property is a fundus scattering rate of the subject's eye, and
wherein the determination unit determines a threshold value of an output of the imaging unit as the parameter to a value higher than a reference threshold value in a case where the fundus scattering rate is higher than a reference scattering rate.

7. The ophthalmologic apparatus according to claim 1,
wherein the physical property is a diopter of the subject's eye, and
wherein the determination unit increases an amount of the illumination light as the parameter in a case where the diopter is myopic.

8. The ophthalmologic apparatus according to claim 7, wherein, if the subject's eye is a myopic eye according to a result of preliminary measurement of an eye refractive power, the determination unit determines an illumination light amount parameter for adjusting an illumination light amount so as to compensate for a reduction in an imaging light amount due to a distant position of a fundus compared to a fundus of a hyperopic eye.

9. The ophthalmologic apparatus according to claim 1, wherein the determination unit determines a threshold value parameter for calculating a barycentric position of the image of the light flux, a color conversion parameter for converting a color of the image of the subject's eye, or a illumination light amount parameter for adjusting an illumination light amount according to a luminance or a hue of an iris of the subject's eye, which varies depending on a race of a subject.

10. The ophthalmologic apparatus according to claim 9, wherein the determination unit includes an anterior eye imaging unit configured to image an anterior eye of the subject's eye by infrared light or visible light, and a detection unit configured to detect the luminance or the hue of the iris of the subject's eye imaged by the anterior eye imaging unit.

11. The ophthalmologic apparatus according to claim 10, wherein the determination unit detects the luminance of the iris of the subject's eye based on an output of the anterior eye imaging unit when the anterior eye of the subject's eye is illuminated with a constant illumination light amount.

12. The ophthalmologic apparatus according to claim 9, wherein, if the subject is a Westerner, the determination unit determines the threshold value parameter higher than that used in the case of the subject being a Japanese person, or determines the color conversion parameter in such a manner that a background color becomes the same as or similar to a background color when the subject is a Japanese person.

13. An ophthalmologic control method comprising:
capturing an image of a subject's eye by using an imaging unit and returned light from the subject's eye irradiated with illumination light;
determining a parameter for acquiring unique information of the subject's eye based on a physical property of the subject's eye; and
acquiring the unique information based on the determined parameter and an output of the imaging unit.

14. A non-transitory computer-readable storage medium storing a program that causes a computer to execute the ophthalmologic control method according to claim 13.

15. The ophthalmologic control method according to claim 13,
wherein the physical property is a fundus scattering rate of the subject's eye, and
wherein a threshold value of an output of the imaging unit is determined as the parameter to a value higher than a reference threshold value in a case where the fundus scattering rate is higher than a reference scattering rate.

16. The ophthalmologic control method according to claim 13,
wherein the physical property is a diopter of the subject's eye, and
wherein the determination unit increases a light amount of the illumination light as the parameter in a case where the diopter is myopic.

17. An ophthalmologic apparatus comprising:
a determination unit configured to determine a threshold value of an output of an imaging unit which captures an image of a subject's eye; and
an acquisition unit configured to acquire eye refractive power information of the subject's eye based on the determined threshold value and an output of the imaging unit.

18. The ophthalmologic apparatus according to claim 17, wherein the determination unit determines, as the threshold value, a value which is higher than a reference threshold value in a case where a fundus scattering rate of the subject's eye is higher than a reference scattering rate.

19. An ophthalmologic control method comprising:
determining a threshold value of an output of an imaging unit which captures an image of a subject's eye; and
acquiring eye refractive power information of the subject's eye based on the determined threshold value and an output of the imaging unit.

20. A non-transitory computer-readable storage medium storing a program that causes a computer to execute the ophthalmologic control method according to claim 19.

21. The ophthalmologic control method according to claim 19, wherein a value which is higher than a reference threshold value is determined as the threshold value in a case where a fundus scattering rate of the subject's eye is higher than a reference scattering rate.

* * * * *